United States Patent [19]

Shibasaki et al.

[11] Patent Number: 5,081,238
[45] Date of Patent: Jan. 14, 1992

[54] βMETHYL AZETIDINONE DERIVATIVES AND STEREOSELECTIVE PROCESS FOR PREPARING THE SAME

[75] Inventors: Masakatsu Shibasaki, Mitaka; Takamasa Iimori, Sagamihara, both of Japan

[73] Assignee: Sagami Chemical Research Center, Tokyo, Japan

[21] Appl. No.: 535,223

[22] Filed: Jun. 8, 1990

Related U.S. Application Data

[63] Continuation of Ser. No. 303,033, Jan. 27, 1989, abandoned, which is a continuation of Ser. No. 923,999, Oct. 28, 1986, abandoned.

[30] Foreign Application Priority Data

Oct. 29, 1985 [JP] Japan ................. 60-240540

[51] Int. Cl.⁵ ............ C07D 205/08; C07B 53/00
[52] U.S. Cl. ............................... 540/200
[58] Field of Search ........................ 540/200

[56] References Cited

U.S. PATENT DOCUMENTS

| | | | |
|---|---|---|---|
| 3,859,319 | 1/1975 | Mrowca | 560/207 |
| 3,904,672 | 9/1975 | Khifton | 560/207 |
| 4,055,721 | 10/1977 | Kawata | 560/207 |
| 4,082,810 | 4/1978 | Brown | 260/606.5 |

FOREIGN PATENT DOCUMENTS

| | | |
|---|---|---|
| 0071908 | 2/1983 | European Pat. Off. . |
| 0113101 | 11/1984 | European Pat. Off. . |
| 0180189 | 5/1986 | European Pat. Off. . |
| 189189 | 5/1986 | European Pat. Off. . |
| 0192171 | 8/1986 | European Pat. Off. . |
| 51-80814 | 7/1976 | Japan . |
| 2919912 | 6/1969 | U.S.S.R. ............. 560/207 |

OTHER PUBLICATIONS

Patent Abstracts of Japan, vol. 9, No. 180 (C-293) [1903], 25th Jul 1985 & JP-A-60 51171 (Sankyo K.K.) 22-03-1985.
Houben-Weyl "Methoden der Organischen Chemie", vol. V/2a, 1977, pp. 797-805, Georg Thieme Verlag, Stuttgart; V. Jager et al., "Alkine", p. 804.
Chamberlin, J. Amer. Chem. Soc. 107, 1440 (1985).
Ganem, J. Org. Chem 40, 146 (1975).
Brown et al., J. Amer. Chem. Soc. 94, 7159 (1972).
Ozaki, Chem. Abs. 86, 55173q (1976).
Mori, Chem. Letters 1975, pp. 39-42.
Ganem et al., J. Org. Chem. 40, 2846.
Midland, Chem. Abs. 102, 78464 (1984).
Smimagaki, Chem. Abs. 102, 78464 (1984).
Hutchins, Chem. Abs. 101, 6662(1984).

*Primary Examiner*—Mark L. Berch
*Attorney, Agent, or Firm*—Armstrong, Nikaido, Marmelstein, Kibovcik & Murray

[57] ABSTRACT

An azetidinone derivative having the general formula (I):

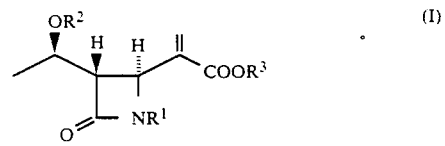

wherein $R^1$ and $R^2$ are hydrogen atom or a protective group and $R^3$ is an alkyl group or hydrogen atom, a process for preparing the same, and a process for preparing an azetidinone derivative having the general formula (II):

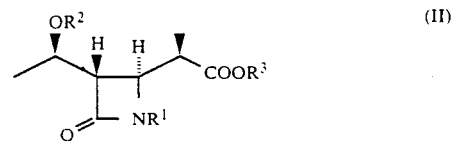

wherein $R^1$, $R^2$ and $R^3$ are as above. The azetidinone derivative (I) of the present invention can be converted into an important intermediate of 1β-methylcarbapenem antibiotics of a selective reduction of the double bond.

12 Claims, No Drawings

βMETHYL AZETIDINONE DERIVATIVES AND STEREOSELECTIVE PROCESS FOR PREPARING THE SAME

This application is a continuation of application Ser. No. 303,033 filed Jan. 27, 1989, now abandoned is a continuation of application Ser. No. 923,999 filed Oct. 28, 1986, now abandoned.

BACKGROUND OF THE INVENTION

The present invention relates to an azetidinone derivative having the general formula (I):

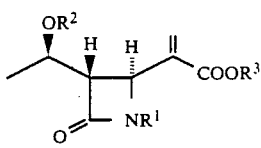

wherein $R^1$ and $R^2$ are hydrogen atom or a protective group and $R^3$ is an alkyl group or hydrogen atom, a process for preparing the same, and a process for preparing an azetidinone derivative having the general formula (II):

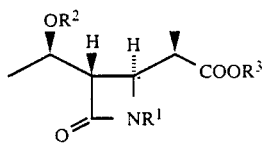

wherein $R^1$, $R^2$ and $R^3$ are as above.

The azetidinone derivative (I) of the present invention can be converted into an important intermediate of 1β-methylcarbapenem antibiotics by a selective reduction of the double bond (cf. the following Reference Examples). The 1β-methylcarbapenem antibiotics show an excellent antibacterial activity against almost all kinds of bacteria including Psendomonas aeruginosa with much more powerful activity than that of known drugs and an excellent stability against β-lactamase. Moreover, the 1β-methylcarbapenem antibiotics also have a metabolic stability, which was not obtained in case of the carbapenem antibiotics, and thus are greatly expected to be the β-lactam antibiotics of the fourth generation.

It is well known that β-lactam compound having the general formula (II):

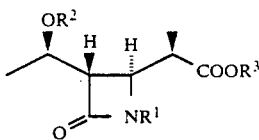

wherein $R^1$, $R^2$ and $R^3$ are as above, is a main intermediate for synthesizing 1β-methylcarbapenem antibiotics. The conventional methods, however, cannot synthesize 1β methyl group stereo-selectively and requires extremely troublesome procedures for separating stereoisomers (for example, D. H. Shih, F. Baker, L. Cama, and B. G. Christensen, Heterocycles, 21, 1 (1984); D. H. Shih, J. A. Fayter, L. D. Cama, B. G. Christensen, and J. Hirshfield, Tetrahedron Lett., 26, 583 (1985); D. H. Shir, L. Cama and B. G. Christensen, ibid., 26, 587 (1985); T. Shibata, K. Iino, T. Tanaka, T. Hashimoto, Y. Kameyama, and Y. Sugimura; ibid., 26, 4739 (1985)).

As a result of the present inventors' effort to solve the above-mentioned problem, it was found that the azetidinone derivative having the general formula (I) can be a very effective intermediate for synthesizing the above β-lactam compound having the general formula (II).

It may be said that the industrial synthesis of the 1β-methylcarbapenem antibiotics becomes easier by the present invention.

SUMMARY OF THE INVENTION

According to the present invention, there are provided an azetidinone derivative having the general formula (I):

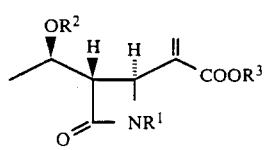

wherein $R^1$, $R^2$ and $R^3$ are above, a process for preparing the same, which comprises hydroalkoxycarbonylating an ethynylazetidinone having the general formula (III):

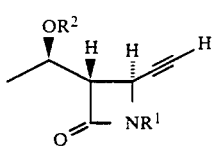

in the presence of group VIII metal or metal compound, alcohol and carbon monoxide, and then, if necessary, hydrolyzing the obtained product, a process for preparing an azetidinone derivative having the general formula (II):

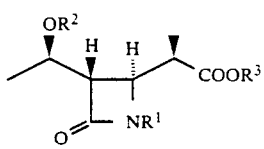

which comprises reducing an azetidinone derivative having the general formula (I) in the presence of L-SELECTRIDE®, and a process for preparing an azetidinone derivative having the general formula (II), which comprises hydroalkoxycarbonylating an ethynylazetidinone having the general formula (III) in the presence of group VIII metal or metal compound, alcohol and carbon monoxide and, if necessary, hydrolyzing the obtained product to give an azetidinone derivative having the general formula (I), which is then reduced in the presence of L-SELECTRIDE®.

DETAILED DESCRIPTION OF THE INVENTION

The starting material of the present invention, the ethynylazetidinone having the general formula (III) can be prepared from β-hydroxybutyric acid thiol ester having the general formula (IV):

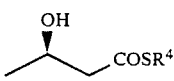

wherein R⁴ is an alkyl group or an aryl group, or according to the methods described in the literature (T. Chiba and T. Nakai, Chem. Lett., 651 (1985), D. C. Ha, D. J. Hart, and T. K. Yang, J. Am. Chem. Soc., 106, 4819 (1984)) highly efficiently (cf. the following Reference Examples).

In the general formula (VII) of the starting compound of the present invention, $R^1$ is hydrogen atom or a protective group such as trimethylsilyl group, triethylsilyl group, t-butyldimethylsilyl group, diphenyl-t-butylsilyl group, benzyl group, 4-methoxybenzyl group, 2,4-dimethoxybenzyl group, 4-metthoxyphenyl group, 3,4-dimethoxyphenyl group or 3,4,5-trimethoxyphenyl group, $R^2$ is hydrogen atom or a protective group such as triethylsilyl group, tetrahydropyranyl group, t-butyldimethylsilyl group, 1-ethoxyethyl group, diphenyl-t-butylsilyl group, methoxymethyl group, 1-methyl-1-methoxyethyl group, 4-methoxytetrahydropyranyl group, methyl group, benzyl group, 4-methoxybenzyl group, benzoyl group, acetyl group, β-methoxyethoxymethyl group, benzyloxycarbonyl group, 4-nitrobenzyloxycarbonyl group or 4-methoxybenzyloxycarbonyl group.

The essential condition of the process of the present invention is the hydroalkoxycarbonylation of the ethynylazetidinone having the general formula (III) in the presence of group VIII metal or metal compound, alcohol and carbon monoxide. Examples of the group VIII metal or metal compound are, for instance, palladium black, palladium charcoal, tetrakisphenylphosphine palladium, palladium chloride, nickel carbonyl and the like. Although an amount of the metal or metal compound may vary depending on the other reaction conditions, the reaction proceeds smoothly by employing $10^{-5}$ to 200 molar % of the metal or metal compound. A pressure of carbon monoxide used in the hydroalkoxycarbonylation may range from a normal pressure to 150 atm, preferably from 10 to 50 atm in viewpoint of the reaction efficiency and the operatability. Alcohol is generally used as a solvent. Examples of the alcohol which can be employed in the present invention are, for instance, methanol, ethanol, n-propanol, 1-propanol, n-butanol, sec-butanol, benzylalcohol and the like. In addition to the alcohol, supplementary solvent can also be employed. Examples of such solvent are halogenated hydrocarbons such as methylene chloride, chloroform, carbon tetrachloride and dichloroethane, aromatic organic solvents such as benzene and toluene, ethereal organic solvent such as diethyl ether and tetrahydrofuran, aliphatic hydrocarbons such as pentane and hexane, esters such as ethyl acetate and methyl propionate, acetonitrile, hexamethyl-phosphoric triamide, dimethylsulfoxide, dimethylformamide, water and the like. Although the reaction temperature may vary depending on the other reaction conditions, the reaction usually proceeds at a temperature of from room temperature to 200° C. In some case, the addition of the mineral acid extremely increases the reaction efficiency. Examples of such mineral acid are, for instance, hydrochloric acid, hydrobromic acid, hydroiodic acid and the like. An amount of the mieral acid employed may range from 10 to 200 molar %.

The azetidinone derivative as prepared easily by the above method can be converted into the β-lactam compound having the general formula (II) with a high selectivity by means of a reducing agent such as L-SELECTRIDE ®. L-SELECTRIDE ® is a trademarked product of Aldrich Chemical Co. Inc., which is lithium tri-sec-butyl-borohydride, 1.0M solution in tetrahydryofuran.

Among the compounds having the general formula (I), the compound in the form of free acid can be easily obtained by hydrolyzing the corresponding ester according to the usual procedure.

The present invention is more particularly described and explained by the following Reference Examples and Examples. However, it should be understood that the present invention is not limited to such Reference Examples and Examples and various changes and modifications can be made without departing from the scope of the present invention.

REFERENCE EXAMPLE 1

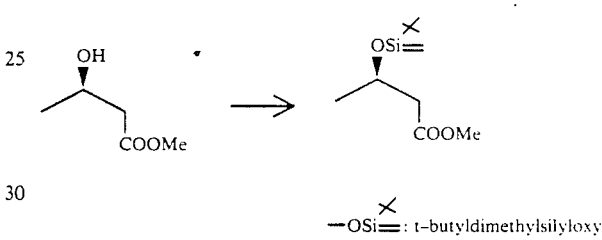

—OSi≡: t-butyldimethylsilyloxy 5.91 Grams (50 mmol) of methyl 3-hydroxybutyrate and 3.74 g (55 mmol) of imidazole were dissolved in 20 ml of DMF and thereto 8.29 g (55 mmol) of t-butyldimethylsilylchloride was added in several portions. After stirring the mixture at room temperature for 30 minutes, ice water was added and extraction with diethyl ether was conducted three times. The extract was washed with a saturated solution of NaCl, dried with anhydrous magnesium sulfate and concentrated under reduced pressure. The concentrate was distilled (62° to 68° C./5 mmHg) to give 10.51 g of methyl (—)-3-t-butyldimethylsilyloxybutyrate (yield: 91%).

TLC: 0.4 (hexane:diethyl ether 20:1)
IR: (neat) 1735 cm$^{-1}$
MNR: δ 0.03, 0.06 (each 3H; s), 0.85 (9H; s), 1.20 (3H; d J=5), 2.42 (2H; m), 3.75 (3H; s) and 4.25 (1H; m)
MS: 115, 133, 159 [M-(Me+COOMe)], 175 [M-Bu] and 217 [M-Me]
$[\alpha]_D^{20}$ −31.75° (c=1.94, CHCl₃)

REFERENCE EXAMPLE 2

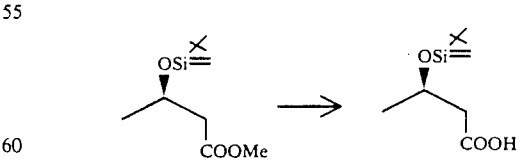

To a solution of 3.58 g (15.4 mmol) of methyl (—)-3-t-butyldimethylsilyloxybutyrate dissolved in 30 ml of methanol, 30 ml of 1N potassium hydroxide was added and the mixture was stirred for 15 hours. After almost all methanol was distilled away, the resultant was acidified with 1N hydrochloric acid and extracted with diethyl ether. The extract was washed with a saturated solution of NaCl, dried with anhydrous magnesium sulfate and concentrated under reduced pressure to give 3.18 g of (−)-3-t-butyldimethylsilyloxybutyric acid (yield: 95%).

TLC: 0.2 (hexane:diethyl ether 20:1)

IR: (neat) 1710 cm$^{-1}$

NMR: δ 0.09 (6H; s), 0.88 (9H; s), 1.20 (3H; d J=6), 2.46 (2H; d J=6) and 4.27 (1H; d t J=6.6)

MS: 110, 137, 197 and 218 [M]

$[\alpha]_D^{20}$ −12.50°) (c=0.96, chloroform)

REFERENCE EXAMPLE 3

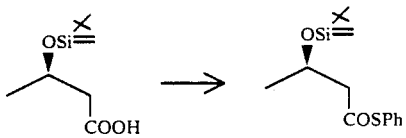

To a solution of 3.18 g (19.2 mmol) of (−)-3-t-butyldimethylsilyloxybutyric acid and 2.26 ml (22 mmol) of thiophenol dissolved in 100 ml of methylene chloride, 4.53 g (22 mmol) of N,N'-dicyclohexylcarbodiimide was added. After stirring the mixture at room temperature for 2 hours, the resultant was filtered and the filtrate was concentrated and distilled (110° to 116° C./0.3 mmHg) to give 5.00 g of (−)-3-t-butyldimethylsilyloxybutyric acid phenylthio ester (yield: 83%).

TLC: 0.3 (hexane:diethyl ether 20:1)

IR: (neat) 1710 cm$^{-1}$

NMR: δ 0.07 (6H; s), 0.91 (9H; s), 1.22 (3H; d J=5), 2.61, 2.87 (each 1H; dd J=15, 7), 4.34 (1H; m) and 7.41 (5H; s)

MS: 115, 159 [M-(Me+COSPh)], 253 [M-Bu] and 295 [M-Me]

$[\alpha]_D^{20}$ −65.91° (c=0.98, CHCl$_3$)

REFERENCE EXAMPLE 4

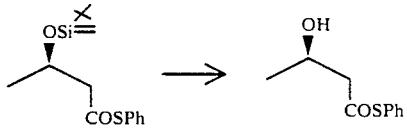

To 3.26 g (10.4 mmol) of (−)-3-t-butyldimethylsilyloxybutyric acid phenylthio ester was added 50 ml of acetic acid: THF:water (3:1:1) and the mixture was stirred at 50° C. for 24 hours. The resultant was concentrated and distilled (128° to 130° C./0.8 mmHg) to give 1.91 g of (−)-3-hydroxybutyric acid phenylthio ester (yield: 94%).

TLC: 0.35 (hexane:diethyl ether 1:1)

IR: (neat) 3440 and 1705 cm$^{-1}$

NMR: δ 1.20 (3H; d J=6), 2.82 (2H; d J=6), 3.0 (1H; br. s), 4.22 (1H; m) and 7.36 (5H; s)

MS: 110 [PhSH], 137 [COSPh] and 196 [M]

$[\alpha]_D^{20}$ −42.25° (c=1.42, CHCl$_3$)

REFERENCE EXAMPLE 5

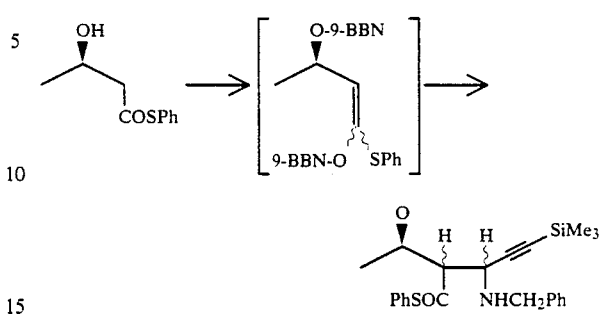

A mixture of 1.51 g (12.0 mmol) of 3-trimethylsilyl-2-propinal, 1.31 ml (12.0 mmol) of benzylamine and 10 ml of diethyl ether was stirred for 30 minutes and the solvent was distilled away under reduced pressure. The residue was distilled under reduced pressure (120° to 130° C. of oil bath temperature/1 mmHg) and the obtained imine was used as it is in the following reaction.

To a solution of 1.963 g (10.0 mmol) of (−)-3-hydroxybutyric acid phenylthio ester dissolved in 40 ml of methylene chloride, 4.00 ml (23.0 mmol) of diisopropylethylamine and 5.94 g (22.0 mmol) of 9-BBN trifurate were added at −78° C. After the mixture was heated to −25° C. for 1 hour and stirred at −30° to −20° C. for 1 hour, 40 ml of the methylene chloride solution of the previously prepared imine was added dropwise at the same temperature for about 20 minutes. The mixture was heated to room temperature for 1.5 hours and further stirred for 1 hour. After the reaction solution was cooled to −35° to −40° C., a mixture of 60 ml of phosphate buffer (pH 7.0), 60 ml of methanol and 30 ml of 31% hydrogen peroxide was added for about 20 minutes. After the mixture was heated to 0° C. for 30 minutes and stirred vigorously at room temperature for 1 hour, the resultant was extracted twice with methylene chloride. The extract was washed with a saturated solution of NaCl, dried with anhydrous magnesium sulfate and concentrated under reduced pressure. The concentrate was purified with silica-gel column (C-300; developer hexane:diethyl ether 3:2) to give 2.054 g of 3-benzylamino-2-(1-hydroxyethyl)-5-trimethylsilyl-4-pentynic acid phenylthio ester (yield: 50%).

TLC: 0.41 (hexane:diethyl ether 3:2)

IR: (neat) 3400, 2160 and 1700 cm$^{-1}$

NMR: δ 0.23 (3H; s), 1.25 (3H; d J=7), 2.92 (1H; t J=6), 3.6 to 3.8 (2H; m), 4.03 (1H; d J=12), 4.3 (1H; m), 7.30 (5H; s) and 7.39 (5H; s)

MS: 151, 216, 302 [M$^+$-SPh] and 412 [M$^+$+1]

REFERENCE EXAMPLE 6

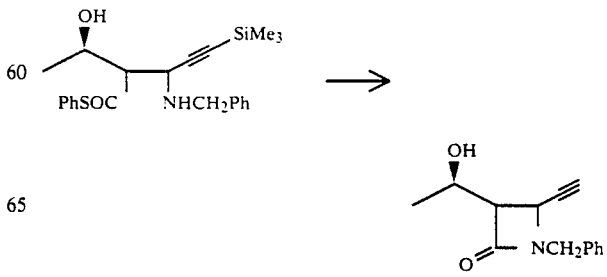

To a solution of 2.054 g (5.0 mmol) of 3-benzylamino-2-(1-hydroxyethyl)-5-trimethylsilyl-4-pentinic acid phenylthio ester dissolved in 40 ml of THF was added 3 ml of 4N potassium hydroxide and the mixture was stirred at room temperature for 3 hours. The resultant was neutralised with 2N hydrochloric acid and extracted with ethyl acetate six times while conducting salting out. The extract was dried with anhydrous magnesium sulfate and concentrated. To the concentrate were added 250 ml of acetonitrile and then 1.57 g (6.0 mmol) of triphenylphosphine and the mixture was vigorously stirred under reflux condition, to which a solution of 1.32 g (6.0 mmol) of 2,2'-dipyridyldisulfide in 50 ml of acetonitrile was added dropwise for 40 minutes. After reflux for 1 hour, the reaction solution was concentrated and purified twice with 50 g of silica-gel chromatography (developer methylene chloride→diethyl ether) and then with 50 g of silica-gel chromatography (developer hexane:diethyl ether 1:4) to give 801 mg of trans-form and 62 mg of cis-form of 1-benzyl-4-ethynyl-3-(1-hydroxyethyl)-2-azetidinone.

For analysis of the trans-form, sample obtained by recrystallization from diethyl ether was employed:

Trans-form

TLC 0.75 (diethyl ether)
mp: 134° C.
IR: (chloroform) 3450 and 1745 cm$^{-1}$
NMR: δ 1.24 (3H; d J=6), 2.42 (1H; d J=1), 2.7 (1H; br. s), 3.28 (1H; dd J=5, 2.5), 4.1 (3H; m), 4.73 (1H; d J=15) and 7.29 (5H; s)
MS: 132, 186, 211 and 229 [M+]
Elemental Analysis: for $C_{14}H_{15}O_2N$; Calcd.(%): C 73.34, H 6.59, N 6.11; Found (%): C 73.45, H 6.54, N 6.10
$[\alpha]_D^{20}$ −20.45° (c=1.00, chloroform)

Cis-form

TLC: 0.56 (diethyl ether)
IR: (chloroform) 3500 and 1750 cm$^{-1}$
NMR: δ 1.36 (3H; d J=6), 2.68 (1H; d J=2), 2.7 (1H; br. s), 3.27 (1H; dd J=5, 6), 4.2 (3H; m), 4.76 (1H; d J=15) and 7.38 (5H; s)
MS: 150, 187, 205 and 229 [M+]
$[\alpha]_D^{20}$ −58.82° (c=1.22, chloroform)

REFERENCE EXAMPLE 7

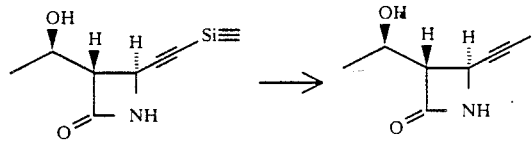

To a solution of 578 mg (2.74 mmol) of 3-(1-hydroxyethyl)-4-(2-trimethylsilylethynyl)-2-azetidinone, which was prepared according to T. Chiba and T. Nakai [Chem. Lett., 651 (1985)], in 5 ml of THF, 4 ml (4 mmol) of a 1M solution of tetrabutylammonium fluoride in THF was added. After stirring at room temperature for 2 hours, 10 g of silica-gel was added, the solvent was distilled away and the resultant was eluted with diethyl ether. The eluent was concentrated and purified with 10 g of silica-gel column (diethyl ether) to give 347 mg of 4-ethynyl-3-(1-hydroxyethyl)-2-azetidinone (yield: 92%).

TLC: 0.35 (diethyl ether)
IR: (neat) 3300 and 1750 cm$^{-1}$
NMR: δ 1.28 (3H; d J=6), 2.45 (1H; d J=2), 3.3 (2H; m), 4.2 (1H; m), 4.28 (1H; t J=2) and 6.8 (1H; m)
MS: 106, 121 (M+-H$_2$O) and 139 (M+)

REFERENCE EXAMPLE 8

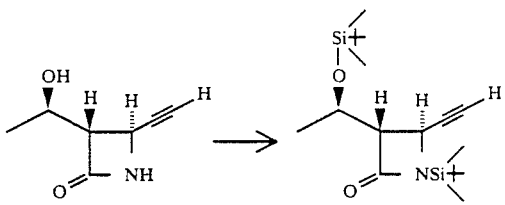

To a solution of 63 mg (0.45 mmol) of 4-ethynyl-3-(1-hydroxyethyl)-2-azetidinone in 2 ml of DMF, 0.17 ml (1.2 mmol) of triethylamine and 180 mg (1.2 mmol) of t-butyldimethylsilyl chloride were added and the mixture was stirred at room temperature for a night. Ice water was added to the reaction solution and the resultant was extracted three times with diethyl ether, washed with a saturated solution of NaCl, dried with anhydrous magnesium sulfate and purified with 5 g of silica-gel column (hexane:ether 10:1) to give 143 mg of 1-t-butyldimethylsilyl-3-(1-t-butyldimethylsilyloxyethyl)-4-ethynyl-2-azetidinone (yield: 87%).

TLC: 0.3 (hexane:ether 10:1)
IR: (chloroform) 1740 cm$^{-1}$
NMR: δ 0.02, 0.04 (each 3H; s), 0.21, 0.23 (each 3H; s), 0.82 (9H; s), 0.91 (9H; s), 1.18 (3H; d J=6), 2.38 (1H; d J=2), 3.23 (1H; t J=2.5) and 4.2 (2H; m)
MS: 148, 153, 310 (M+-Bu) and 352 (M+-Me)

REFERENCE EXAMPLE 9

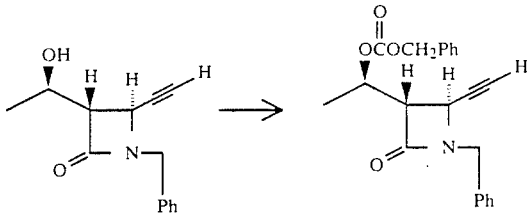

To a solution of 36 mg (0.16 mmol) of 1-benzyl-4-ethynyl-3-(1-hydroxyethyl)-2-azetidinone in 2 ml of methylene chloride, 30 mg (0.25 mmol) of 4,4-dimethylaminopyridine and 0.04 ml (0.25 mmol) of benzyloxycarbonyl chloride were added at −10° C. and the mixture was stirred for a night. Ice water was added to the reaction solution and the resultant was extracted three times with methylene chloride. The extract was washed with a saturated solution of NaCl, dried with anhydrous magnesium sulfate, concentrated and purified with 5 g of silica-gel column (hexane:ether 2:3) to give 40 mg of 1-benzyl-3-(1-benzyloxycarbonyloxyethyl)-4-ethynyl-2-azetidinone (yield: 69%).

TLC: 0.5 (hexane:ether 1:1)
IR: (chloroform) 1760 and 1265 cm$^{-1}$
NMR: δ 1.39 (3H; d J=6), 2.44 (1H; d J=2), 3.48 (1H; dd J=2, 6), 4.0 (2H; m), 4.79 (1H; d J=15), 5.1 (3H; m), 7.28 (5H; s) and 7.42 (5H; s)
MS: 108, 210, 228, 272 (M+-PhCH$_2$), 318, 335 and 363

EXAMPLE 1

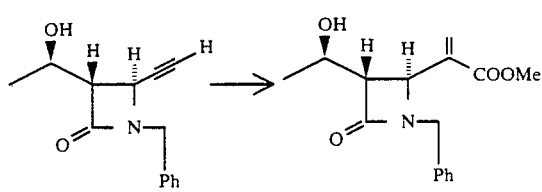

In autoclave were introduced 229 mg (1 mmol) of 1-benzyl-4-ethynyl-3-(1-hydroxyethyl)-2-azetidinone, 10 mg (0.1 mmol) of palladium black, 0.19 ml (0.5 mmol) of concentrated hydroiodic acid and 10 ml of methanol. The autoclave was charged with carbon monoxide at 20 atm and the reaction was carried out at 65° C. for 16 hours. To the reaction mixture was added 0.2 ml of triethylamine and the mixture was concentrated under reduced pressure. The concentrate was purified with 15 g of silica-gel column (benzene:ethyl acetate 3:2) to give 203 mg of 1-benzyl-3-(1-hydroxyethyl)-4-(1-methoxycarbonylethenyl)-2-azetidinone (yield: 70%).

TLC: 0.3 (benzene:ethyl acetate 1:1)

IR: (chloroform) 3500 and 1745 cm$^{-1}$

NMR: $\delta$ 1.28 (3H; d J=6), 2.96 (1H; dd J=2, 6), 3.3 (1H; br. s), 3.74 (3H; s), 3.91 (1H; d J=15), 4.1 (2H; m), 4.79 (1H; d J=15), 5.85 (1H; s), 6.36 (1H; s) and 7.3 (5H; s)

MS: 156, 177, 216, 271 (M$^+$-H$_2$O) and 290 (M$^+$+1)

EXAMPLE 2

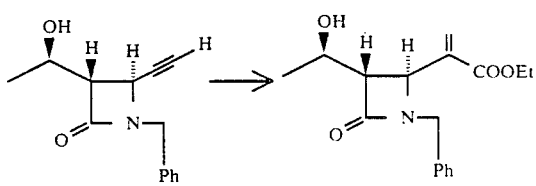

In autoclave were introduced 46 mg (0.2 mmol) of 1-benzyl-4-ethynyl-3-(1-hydroxyethyl)-2-azetidinone, 5 mg (0.05 mmol) of palladium black, 0.02 ml (0.1 mmol) of concentrated hydroiodic acid and 5 ml of ethanol. The autoclave was charged with carbon monoxide at 20 atm and the reaction was carried out at 65° C. for 12 hours. To the reaction mixture was added 0.1 ml of triethylamine and the mixture was concentrated under reduced pressure. The concentrate was purified with 2 g of silica-gel column (benzene:ethyl acetate 3:2) to give 32 mg of 1-benzyl-3-(1-hydroxyethyl)-4-(1-methoxycarbonylethenyl)-2-azetidinone (yield: 53%).

TLC: 0.3 (benzene:ethyl acetate 1:1)

IR: (chloroform) 3300 and 1745 cm$^{-1}$

NMR: $\delta$ 1.3 (5H; m), 2.91 (1H; dd J=2, 6), 3.2 (1H; br. s), 3.90 (1H; d J=15), 4 to 4.5 (4H; m), 4.78 (1H; d J=15), 5.86 (1H; s), 6.34 (1H; s) and 7.3 (5H; s)

MS: 96, 134, 158, 170, 172, 230, 275 and 285

EXAMPLE 3

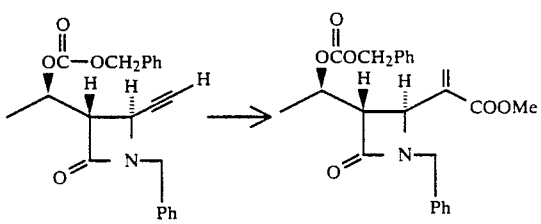

In autoclave were introduced 35 mg (0.1 mmol) of 1-benzyl-3-(1-benzyloxycarbonyloxyethyl)-4-ethynyl-2-azetidinone, 3 mg (0.03 mmol) of palladium black, 0.01 ml (0.05 mmol) of concentrated hydroiodic acid and 4 ml of methanol. The autoclave was charged with carbon monoxide at 20 atm and the reaction was carried out at 65° C. for 12 hours. To the reaction mixture was added 0.1 ml of triethylamine and the mixture was concentrated under reduced pressure. The concentrate was purified with 2 g of silica-gel column (ether:hexane 2:1) to give 31 mg of 1-benzyl-3-(1-benzyloxycarbonyloxyethyl)-4-(1-methoxycarbonylethenyl)-2-azetidinone (yield: 73%).

TLC: 0.4 (ether:hexane 2:1)

IR (chloroform) 1760 and 1265 cm$^{-1}$

NMR: $\delta$ 1.27 (3H; d J=6), 3.20 (1H; dd J=2, 6), 3.63 (3H; s), 3.84 (1H; d J=15), 4.32 (1H; d J=2), 4.76 (1H; d J=15), 5.1 (1H; m), 5.12 (2H; s), 5.72 (1H; s), 6.29 (1H; s), 7.2 (5H; s) and 7.4 (5H; s)

MS: 96, 180, 196, 216, 228, 270, 290, 332 (M$^+$-PhCH$_2$) and 395

EXAMPLE 4

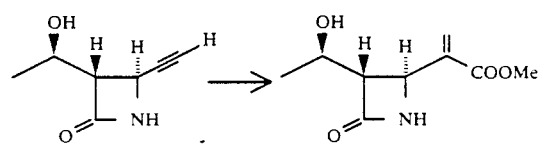

The reaction was carried out as in Example 1 except that 144 mg (1.0 mmol) of 4-ethynyl-3-(1-hydroxyethyl)-2-azetidinone was employed. The obtained product was purified with 10 g of silica-gel column (benzene:acetone 1:1) to give 89 mg of 3-(1-hydroxyethyl)-4-(1--methoxycarbonylethenyl)-2-azetidinone (yield: 45%).

TLC: 0.15 (ether)

IR: (chloroform) 1710 and 1760 cm$^{-1}$

NMR: $\delta$ 1.41 (3H; d J=6), 2.96 (1H; dd J=2, 6), 3.5 (1H; br. s), 3.81 (3H; s), 4.25 (1H; m), 4.47 (1H; m), 5.93 (1H; s), 6.31 (1H; s) and 7.0 (1H; br. s)

MS: 114, 124, 139, 149, 165 and 181 (M$^+$-H$_2$O)

EXAMPLE 5

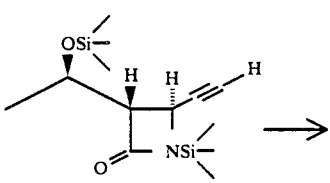

-continued

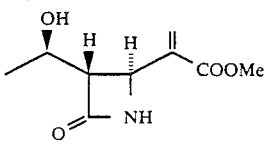

In autoclave were introduced 184 mg (0.5 mmol) of 1-t-butyldimethylsilyl-3-(1-t-butyldimethylsilyloxyethyl)-4-ethynyl-2-azetidinone, 5 mg (0.05 mmol) of palladium black, 0.1 ml (0.25 mmol) of concentrated hydroiodic acid and 5 ml of methanol. The autoclave was charged with carbon monoxide at 20 atm and the reaction was carried out at 65° C. for 16 hours. To the reaction mixture was added 0.1 ml of triethylamine and the mixture was concentrated under reduced pressure. The concentrate was purified with 10 g of silica-gel column (benzene:acetone 1:1) to give 50 mg of 3-(1-hydroxyethyl)-4-(1-methoxycarbonylethenyl)-2-azetidinone (yield: 50%). The spectrum data of the obtained product agreed completely with those of the product obtained in Example 4.

EXAMPLE 6

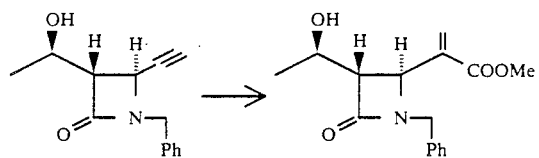

In autoclave were introduced 46 mg (0.2 mmol) of 1-benzyl-4-ethynyl-3-(1-hydroxyethyl)-2-azetidinone, 30 mg of 10% palladium charcoal, 0.02 ml (0.1 mmol) of concentrated hydroiodic acid and 5 ml of methanol. The autoclave was charged with carbon monoxide at 20 atm and the reaction was carried out at 65° C. for 12 hours. To the reaction mixture was added 0.1 ml of triethylamine and the mixture was concentrated under reduced pressure. The concentrate was purified with 2 g of silica-gel column (benzene:ethyl acetate 3:2) to give 6 mg of 1-benzyl-3-(1-hydroxyethyl)-4-(1-methoxycarbonylethenyl)-2-azetidinone (yield: 10%). The spectrum data of the obtained product agreed completely with those of the product obtained in Example 1.

EXAMPLE 7

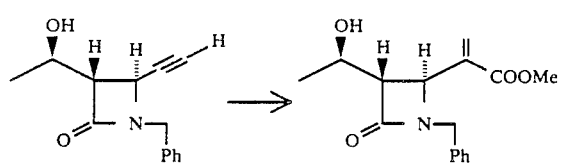

The procedure in Example 6 was repeated except that tetrakistriphenylphosphine was employed in place of 10% palladium charcoal to give 7 mg of 1-benzyl-3-(1-hydroxyethyl)-4-(1-methoxycarbonylethenyl)-2-azetidinone (yield: 12%). The spectrum data of the obtained product agreed completely with those of the product obtained in Example 1.

EXAMPLE 8

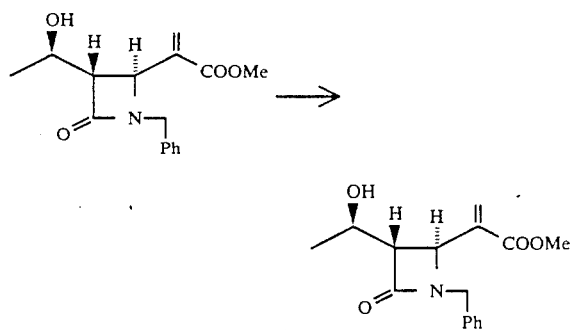

To a solution of 30 mg (0.1 mmol) of 1-benzyl-3-(1-hydroxyethyl)-4-(1-methoxycarbonylethenyl)-2-azetidinone dissolved in 1 ml of methanol, 1 ml (1 mmol) of 1N potassium hydroxide was added with ice bath. After the mixture was stirred at room temperature for 4 hours, 1 ml of 1N hydrochloric acid was added and the extraction with ethyl acetate was conducted three times. The extract was washed with a saturated solution of NaCl, dried with magnesium sulfate and concentrated to give 19 mg of 1-benzyl-4-(1-carboxyethenyl)-3-(1-hydroxyethyl)-2-azetidinone (yield: 68%).

TLC: 0.2 (ethyl acetate)
IR: (neat) 3400 and 1735 cm$^{-1}$
NMR: δ 1.35 (3H; d J=6), 3.06 (1H; dd J=7, 2), 3.8 (1H; m), 4.3 (1H; m), 4.92 (1H; d J=15), 5.93 (1H; s), 6.4 (2H; br. s), 6.48 (1H; s) and 7.44 (5H; s)
MS: 73, 84, 86, 106, 107, 149, 167 and 205

EXAMPLE 9

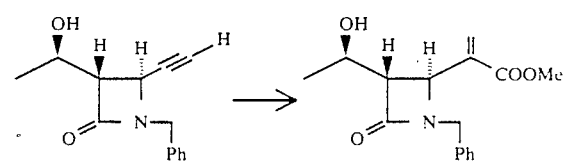

The procedure in Example 2 was repeated except that methanol/diethyl ether (1/1) was employed in place of ethanol to give 30 mg of 1-benzyl-3-(1-hydroxyethyl)-4-(1-methoxycarbonylethenyl)-2-azetidinone (yield: 50%). The spectrum data of the obtained product agreed completely with those of product obtained in Example 1.

REFERENCE EXAMPLE 10

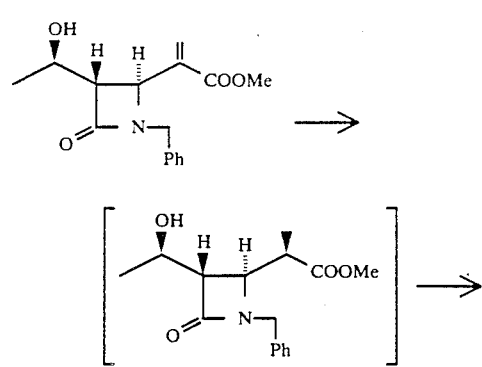

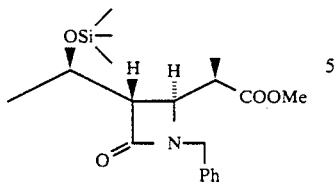

To a solution of 30 mg (0.1 mmol) of 1-benzyl-3-(1-hydroxyethyl)-4-(1-(1-methoxycarbonylethenyl)-2-azetidinone dissolved in 0.5 ml of THF and 1 ml of sec-butanol, 0.5 ml (0.5 mmol) of a 1M solution of L-SELECTRIDE ® in THF was slowly added at −78° C. After stirring at the same temperature for 1 hour, 0.1 ml of acetic acid was added and the mixture was vigorously stirred for 10 minutes. sec-Butanol and acetic acid were removed under reduced pressure by the azeotropic distillation with toluene at room temperature. Ethyl acetate was added to the concentrated residue and the resultant was filtered with selite. The filtrate was concentrated and thereto 1 ml of DMF, 20 mg (0.3 mmol) of imidazole and 45 mg (0.3 mmol) of t-butyldimethylsilylchloride were added successively. After stirring at room temperature for a night, ice water was added and the extraction with ether was carried out. The organic layer was washed with a saturated solution of NaCl, dried with magnesium sulfate and purified with 2 g of silica-gel column (hexane:ether 1:1) to give 29 mg of 1-benzyl-4-(1-methoxycarbonylethyl)-3-(1-t-butyldimethylsilyloxyethyl)-2-azetidinone (yield: 72%). NMR showed α:β=1:8 (cf. the following Reference Examples 11 and 12).

TLC: 0.35 (ether:hexane 1:1)

IR: 1740 cm$^{-1}$

NMR: δ 0.02, 0.05 (each 3H; s), 0.84 (9H; s), 1.09 (3H; d J=7), 1.22 (3H; d J=6), 2.8 (1H; m), 3.06 (1H; dd J=2, 6), 3.61 (2.67 H; s corresponding to β-form of methyl ether), 3.65 (0.33 H; s corresponding to α-form of methyl ester), 3.82 (1H; m), 4.1 (2H; m), 4.68 (1H; d J=15) and 7.3 (5H; s)

MS: 91, 348 (M$^+$-Bu) and 390 (M$^+$-Me)

REFERENCE EXAMPLE 11

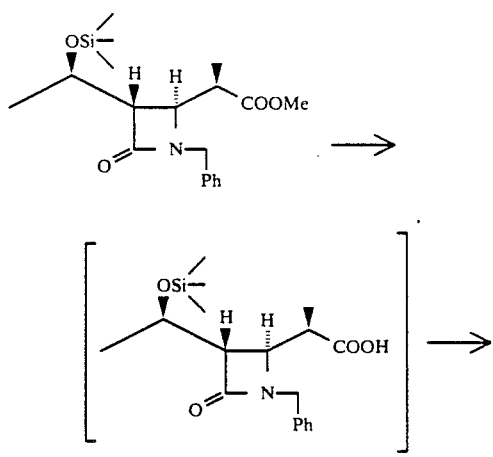

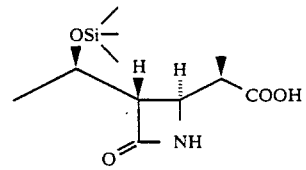

To a solution of 25 mg of 1-benzyl-4-(1-methoxycarbonylethyl)-3-(1-t-butyldimethylsilyoxyethyl)-2-azetidinone, which was obtained in Reference Example 10, dissolved in 1 ml of methanol, 1 ml (1 mmol) of 1N potassium hydroxide was added and the mixture was stirred at room temperature for 6 hours. To the reaction solution was added 1 ml of 2N hydrochloric acid with ice bath and the resultant was extracted with ethyl acetate. The extract was washed with a saturated solution of NaCl, dried with magnesium sulfate and concentrated. The concentrate was dissolved in 1 ml of ether and the solution was added at −78° C. to a blue solution prepared from 20 mg of Na and about 2 ml of ammonia. After stirring at the same temperature for 1 hour, a saturated aqueous solution of ammonium chloride was added to the solution. The mixture was heated to around 0° C. and extracted with ethyl acetate three times. The extract was washed with a saturated solution of NaCl, dried with magnesium sulfate, concentrated and purified with 2 g of silica-gel column (ethyl acetate) to give 14 mg of 3-(1-t-butyldimethylsilyloxyethyl)-4-(1-carboxyethyl)-2-azetidinone (yield: 62%). The spectrum data of the sample obtained by reprecipitation from hexane-methylene chloride agreed completely with those described in the literature [D. H. Shih, F. Baker, L. Cama and B. G. Christensen, Heterocycles 21, 29 (1984)].

REFERENCE EXAMPLE 12

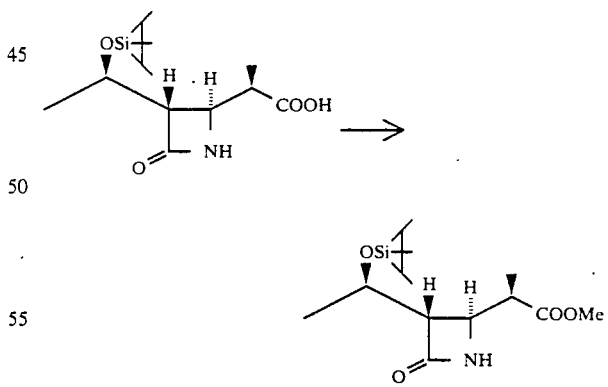

3-(1-t-Butyldimethylsilyloxyethyl)-4-(1-methoxycarbonylethyl)-2-azetidinone was obtained by treating 3-(1-t-butyldimethylsilyloxyethyl)-4-(1-carboxyethyl)-2-azetidinone, which was obtained in Reference Example 11, with diazomethane in ether and proved to be 1β-methyl form by the comparison with the NMR data described in the literature [D. H. Shih, F. Baker, L. Cama and B. G. Christensen, Heterocycles 21, 29 (1984)].

REFERENCE EXAMPLE 13

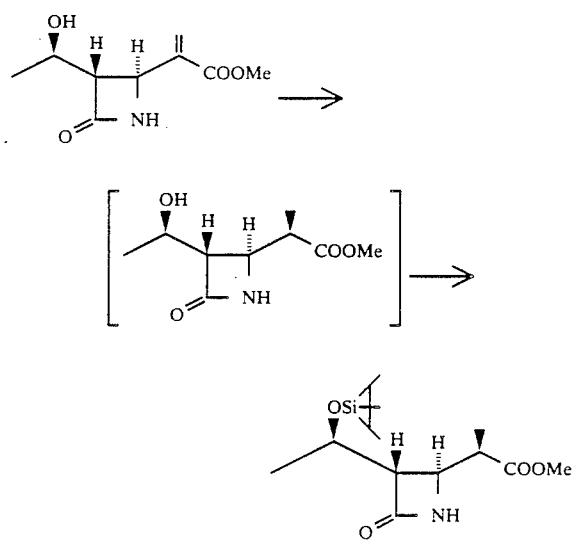

To a solution of 60 mg (0.3 mmol) of 3-(1-hydroxyethyl)-4-(1-methoxycarbonylethenyl)-2-azetidinone dissolved in 2 ml of THF, 10 mg of 5% palladium charcoal was added and the mixture was stirred under hydrogen atmosphere for a night. The reaction solution was filtered with selite and the filtrate was washed with ethyl acetate and concentrated. To the concentrate were added 1 ml of DMF, 40 mg (0.6 mmol) of imidazole and 90 mg (0.6 mmol) of t-butyldimethylsilylchloride and the mixture was stirred for a night. Ice water was added to the reaction solution and the resultant was extracted with ether, washed with a saturated solution of NaCl, dried with magnesium sulfate, concentrated and purified with 15 g of silica-gel column (ether:hexane 1:2→2:3) to give 12 mg of α-form, 16 mg of β-form and 35 mg of the mixture thereof of 3-(1-t-butyldimethylsilyloxyethyl)-4-(1-methoxycarbonylethyl)-2-azetidinone (yield: 67%).

The spectrum data of the obtained compounds agreed completely with those described in the literature [D. H. Shih, F. Baker, L. Cama and B. G. Christensen, Heterocycles 21, 29 (1984)].

REFERENCE EXAMPLE 14

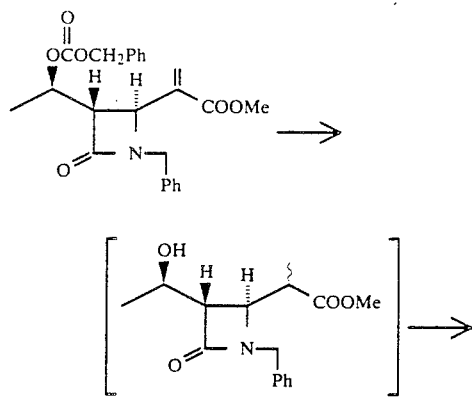

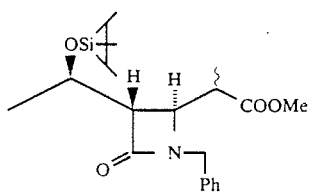

To a solution of 28 mg (0.07 mmol) of 1-benzyl-3-(1-benzyloxycarbonyloxyethyl)-4-(1-methoxycarbonylethenyl)-2-azetidinone dissolved in 2 ml of methanol, 5 mg of 5% palladium charcoal was added and the mixture was stirred under hydrogen atmosphere for a night. The reaction solution was filtered with selite and the filtrate was washed with ethyl acetate and concentrated. To the concentrate were added 1 ml of DMF, 20 mg (0.3 mmol) of imidazole and 45 mg (0.3 mmol) of t-butyldimethylsilylchloride and the mixture was stirred for a night. Ice water was added to the reaction solution and the resultant was extracted with ether, washed with a saturated solution of NaCl, dried with magnesium sulfate, concentrated and purified with 2 g of silica-gel column (hexane:ether 1:1) to give 22 mg of 1-benzyl-4-(1-methoxycarbonylethyl)-3-(1-t-butyldimethylsilyloxyethyl)-2-azetidinone (yield: 84%). Comparison with the NMR data showed α:β=1:1.

TLC, IR and MS were the same as in Reference Example 10.

NMR: δ 0.02, 005 (each 3H; s), 0.84 (9H; s), 1.09 (3H; d J=7), 1.22 (3H; d J=6), 2.4 to 2.9 (3.5H; m), 3.52 (1.5H; s), 3.61 (1.5H; s), 3.65 (0.5H; m), 3.82 (0.5H; s), 3.9 to 4.5 (2.5H; m), 4.68 (0.5H; d J=15) and 7.3 (5H; s)

REFERENCE EXAMPLE 15

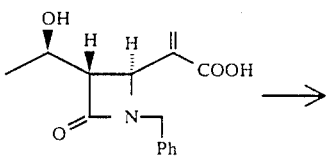

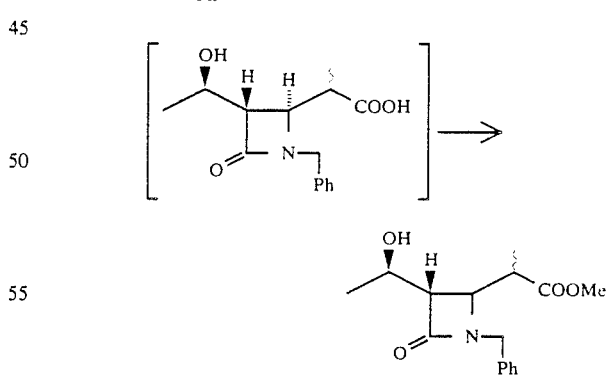

To a solution of 38 mg (0.14 mmol) of 1-benzyl-4-(1-carboxyethyl)-3-(1-hydroxyethyl)-2-azetidinone dissolved in 1 ml of methanol, 5 mg of 5% palladium charcoal was added and the mixture was stirred under hydrogen atmosphere for a night. The reaction solution was filtered with selite, the filtrate was added with an ethereal solution of diazomethane and the resultant was concentrated. The concentrate was purified with 2 g of silica-gel column (benzene:ethyl acetate 1:1) to give 30 mg of 1-benzyl-4-(1-methoxycarbonylethyl)-3-(1-hydroxyethyl)-2-azetidinone (yield: 78%).

TLC: 0.3 (benzene:ethyl acetate 1:1)
IR: (chloroform) 3500 and 1740 cm$^{-1}$
NMR: δ 1.0 to 1.3 (6H; d x 4 each J=ca.6), 2.4 to 3.0 (3H; m), 3.48, 3.51 (total 3H; each s), 3.5 to 4.1 (3H; m), 4.35 (0.5H; m), 4.69 (0.5H; d J=14) and 7.26 (5H; s)
MS: 126, 160, 176, 204, 214, 263 and 292 (M$^+$+1)

REFERENCE EXAMPLE 16

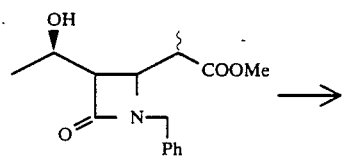

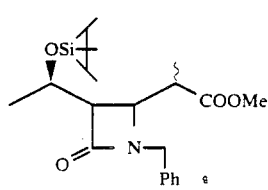

To a solution of 25 mg (0.086 mmol) of 1-benzyl-4-(1-methoxycarbonylethyl)-3-(1-hydroxyethyl)-2-azetidinone, which was obtained in Reference Example 15, dissolved in 1 ml of DMF, were added 20 mg (0.3 mmol) of imidazole and 45 mg (0.3 mmol) of t-butyldimethylsilylchloride and the mixture was stirred for a night. Ice water was added to the reaction solution and the resultant was extracted with ether. The extract was purified with silica-gel column as in Reference Example 14 to give 28 mg of 1-benzyl-4-(1-methoxycarbonylethyl)-3-(1-t-butyldimethylsilyloxyethyl)-2-azetidinone (yield: 81%).

TLC, IR and MS were the same as in Reference Example 10.

NMR nearly agreed with that of Reference Example 14 and the integration ratio of NMR of the methyl ester showed α:β=2:3.

What we claim is:

1. A process for preparing an azetidinone compound of the formula:

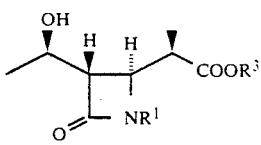

wherein $R^1$ is a protective group and $R^3$ is methyl or ethyl, which comprises stereoselectively reducing the methylene group of compound of the formula:

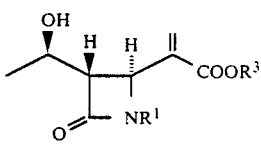

wherein $R^1$ and $R^3$ are as defined above, with L-Selectride in the presence of sec-butanol.

2. The process of claim 1, wherein $R^1$ is benzyl.

3. A process for preparing an azetidinone compound of the formula:

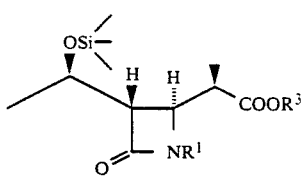

wherein $R^1$ is a protective group and $R^3$ is methyl or ethyl, which comprises stereoselectively reducing the methylene group of the compound of the formula:

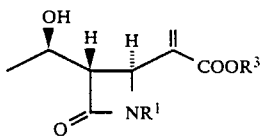

wherein $R^1$ and $R^3$ are as defined above, with L-Selectride in the presence of sec-butanol, and reacting the hydroxyl group of the compound with tert-butyldimethylsilylchloride.

4. The process of claim 3, wherein $R^1$ is benzyl.

5. A process for preparing an azetidinone compound of the formula:

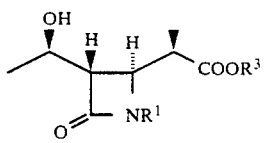

wherein $R^1$ is a protective group and $R^3$ is methyl or ethyl group, which comprises hydromethoxycarbonylating or hydroethoxycarbonylating an ethynylazetidinone of the formula:

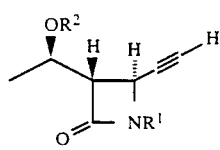

wherein $R^1$ is as defined above, and $R^2$ is hydrogen atom or a protective group, in the presence of palladium black, methanol or ethanol, carbon monoxide and hydrogen iodide, the amount of palladium black being from $10^{-5}$ to 200 molar % based on the ethynylazetidinone, the partial pressure of the carbon monoxide being from 1 to 150 atm, the amount of the hydrogen iodide being from 10 to 200 molar % based on the ethynylazetidinone, at a temperature from room temperature to 200° C., if necessary, hydrolyzing the obtained product to give an intermediate of the formula:

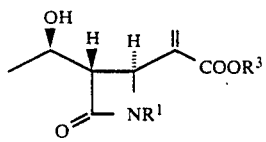

wherein $R^1$ and $R^3$ are as defined above and, stereoselectively reducing the methylene group of the intermediate with L-Selectride in the presence of sec-butanol.

6. The process of claim 5, wherein $R^2$ is hydrogen.

7. The process of claim 5, wherein $R^1$ is benzyl.

8. The process of claim 6, wherein $R^1$ is benzyl.

9. A process for preparing an azetidinone compound of the formula:

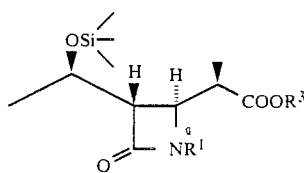

wherein $R^1$ is a protective group and $R^3$ is methyl group or ethyl, which comprises hydromethoxycarbonylating or hydroethoxycarbonylating an ethynylazetidinone having the formula:

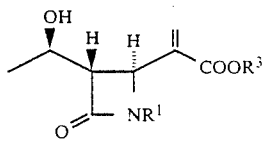

wherein $R^1$ is as defined above and $R^2$ is hydrogen atom or a protective group, in the presence of palladium black, methanol or ethanol, carbon monoxide and hydrogen iodide, the amount of palladium black being from $10^{-5}$ to 200 molar % based on the ethynylazetidinone, the partial pressure of the carbon monoxide being from 1 to 150 atm, the amount of hydrogen iodide being from 10 to 200 molar % based on the ethynylazetidinone, at a temperature from room temperature to 200° C. and, if necessary, hydrolyzing the obtained product to give an intermediate having the formula:

wherein $R^1$ and $R^3$ are as defined above, stereoselectively reducing the intermediate with L-Selectride in the presence of sec-butanol, and reacting the hydroxyl group of the compound with tert-butyldimethylsilylchloride.

10. The process of claim 9, wherein $R^2$ is hydrogen.

11. The process of claim 9, wherein $R^1$ is benzyl.

12. The process of claim 10, wherein $R^1$ is benzyl.

* * * * *